(12) United States Patent
Unger et al.

(10) Patent No.: US 10,166,200 B2
(45) Date of Patent: *Jan. 1, 2019

(54) BUFFERED OXYGEN THERAPEUTICS

(71) Applicant: NuvOx Pharma LLC, Tucson, AZ (US)

(72) Inventors: Evan C. Unger, Tucson, AZ (US); Edmund R. Marinelli, Tucson, AZ (US)

(73) Assignee: NuvOx Pharma LLC, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/617,492

(22) Filed: Jun. 8, 2017

(65) Prior Publication Data
US 2018/0021266 A1 Jan. 25, 2018

Related U.S. Application Data

(63) Continuation of application No. 14/473,945, filed on Aug. 29, 2014, now Pat. No. 9,700,523, which is a continuation-in-part of application No. 13/273,115, filed on Oct. 13, 2011, now Pat. No. 8,822,549.

(51) Int. Cl.
A61K 31/02 (2006.01)
A61K 31/025 (2006.01)
A61K 9/107 (2006.01)
A61K 9/00 (2006.01)

(52) U.S. Cl.
CPC ............ *A61K 31/02* (2013.01); *A61K 9/0026* (2013.01); *A61K 9/107* (2013.01); *A61K 31/025* (2013.01)

(58) Field of Classification Search
CPC ....... A61K 31/02; A61K 9/0026; A61K 9/107
See application file for complete search history.

(56) References Cited

U.S. PATENT DOCUMENTS

| | | | | |
|---|---|---|---|---|
| 8,822,549 B2* | 9/2014 | Johnson | ............... | A61K 31/025 514/53 |
| 9,700,523 B2* | 7/2017 | Unger | ............... | A61K 9/107 |
| 2010/0267842 A1* | 10/2010 | Kiral | ............... | A01N 1/021 514/756 |
| 2013/0096204 A1* | 4/2013 | Johnson | ............... | A61K 31/025 514/759 |

* cited by examiner

*Primary Examiner* — James D. Anderson
(74) *Attorney, Agent, or Firm* — Milstein Zhang & Wu LLC

(57) ABSTRACT

An oxygen therapeutic composition, which includes a perfluorocarbon material having a boiling point of about 4 degrees Celsius to about 60 degrees Celsius, a lipid; a viscosity modifier; a buffer.

4 Claims, 4 Drawing Sheets

BUFFERED OXYGEN THERAPEUTICS

PRIORITY CLAIMS AND RELATED PATENT APPLICATIONS

This application is a continuation of and claims the benefit of priority to U.S. Utility application Ser. No. 14/473,945, filed Aug. 29, 2014, which is a continuation-in-part of and claims the benefit of priority to U.S. Utility application Ser. No. 13/273,115, filed on Oct. 13, 2011, the entire content of each of which is incorporated herein by reference in its entirety.

FIELD OF THE INVENTION

The present invention relates to emulsions of perfluorinated materials useful as oxygen therapeutics.

BACKGROUND OF THE INVENTION

Because blood is prone to viral contamination, and because donated blood has a limited shelf life, donated blood appears to be in constant short supply. In response, much effort has been focused on the development of compositions commonly referred to as "blood substitutes" or "artificial blood". These compositions are appropriately termed "gas carriers."

Microbubbles have been developed for use as contrast-enhancing agents for ultrasonic imaging of the heart and blood vessels. Certain of these contrast-enhancing agent microbubbles are formed from perfluorocarbons ("PFCs") and used in methods for ultrasound imaging. PFCs that are disclosed as being useful for creating microbubbles include dodecafluoro-pentane (DDFP).

SUMMARY OF THE INVENTION

An oxygen therapeutic composition is disclosed. Applicant's oxygen therapeutic composition includes a perfluorocarbon material having a boiling point of about 4 degrees Celsius to about 60 degrees Celsius, a lipid; a viscosity modifier; a buffer; wherein the buffer stabilizes a pH of the composition at pH between about 6.5 to about 7.5, and the composition comprises a viscosity of about 2.0 to about 3.5 mPas. In certain embodiments, the lipid comprises a lipid moiety in combination with a PEG moiety.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE PREFERRED EMBODIMENTS

Figure 1:
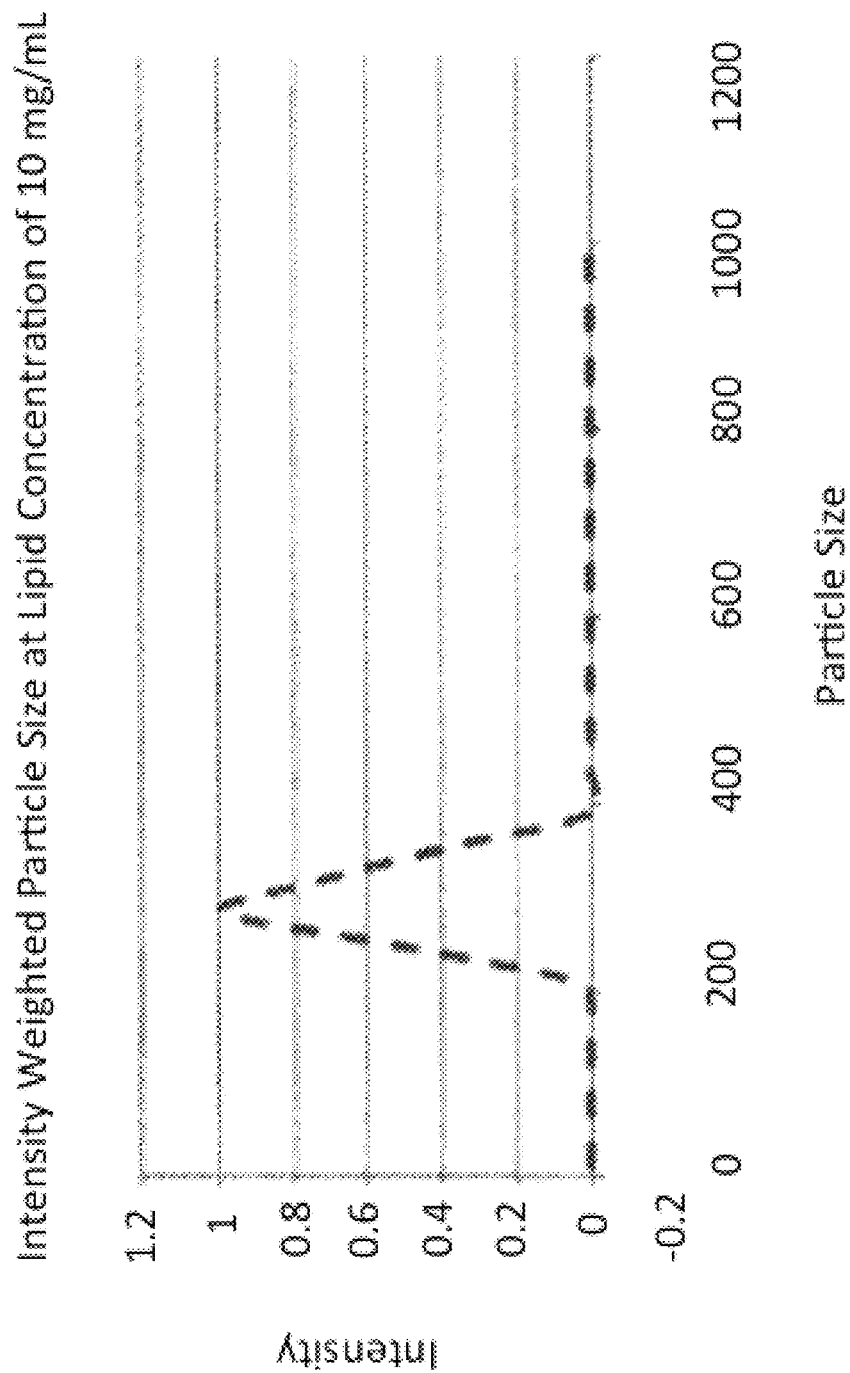
FIG. 1 graphically recites a particle size distribution for Applicants' formulation comprising a lipid concentration of about 10 mg/mL.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

This invention pertains to a surprising discovery pertinent to stabilizing an oxygen therapeutic which in turn is related to another surprising discovery. Microbubbles transport far more oxygen (or other gases) per unit volume than other materials. Liquid perfluorocarbons have been studied extensively as blood replacements or as oxygen therapeutics. They have required high doses and have failed in clinical development. Gaseous fluorocarbons, in the form of microbubbles, however, require less than 1/100th the dose of the liquid fluorocarbons to be effective as oxygen therapeutics.

The invention comprises an emulsion of fluorocarbon useful as an oxygen therapeutic wherein the emulsion is stabilized by PEG-ylated phospholipid. As those skilled in the art will appreciate, "PEG" refers to a polyethylene glycol moiety.

PEG-ylated phospholipid 1 comprises a lipid moiety in combination with a PEG moiety. In the illustrated PEG-ylated phospholipid 1, the lipid moiety comprises dipalmitoylphosphatidylethanolamine, and the PEG moiety comprises PEG having a number average molecular weight of about 5000 Daltons.

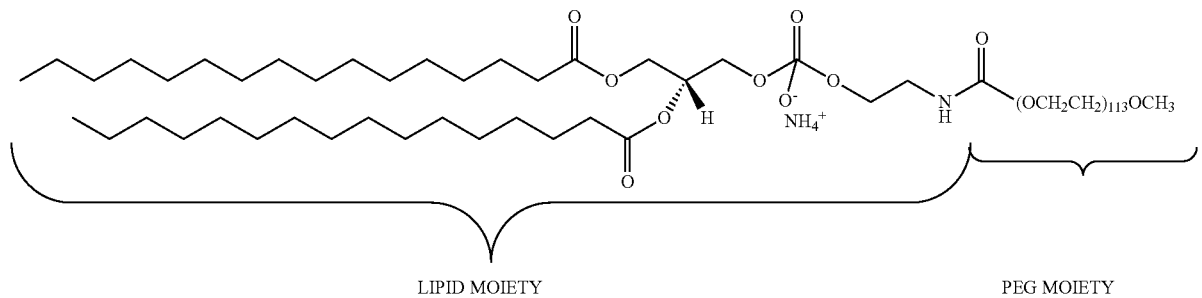

Preferably the emulsion contains two lipids, a neutral phospholipid and a second PEG-ylated phospholipid or a PEG-ylated lipid which is not a phospholipid. The PEG-ylated lipid may comprise between 1% and 100% of the total lipid in the emulsion. In certain embodiments, the PEG-ylated lipid loading is between about 1% and about 20% of the total lipid in the emulsion. In certain embodiments, the PEG-ylated lipid loading is between about 5 and about 10% of the total lipid in the emulsion.

In certain embodiments, the number average molecular weight of the PEG group affixed to the lipid is between about 100 Daltons to about 20,000 Daltons. In certain embodiments, the number average molecular weight of the PEG group affixed to the lipid is between about 1,000 Daltons to about 10,000 Daltons. In certain embodiments, the number average molecular weight of the PEG group affixed to the lipid is between about 2,000 Daltons to about 5,000 Daltons.

In certain embodiments, a non-PEG moiety portion of the lipids in the emulsion comprises from about 10 carbons to about 24 carbons in length. In certain embodiments, the lipids in the emulsion comprise from about 12 carbons to about 22 carbons in length. In certain embodiments, the lipids in the emulsion comprise from about 14 to about 20 carbons in length. Saturated and unsaturated phospholipids (and lipids other than phospholipids) may also be used in the invention and mixtures thereof.

In certain embodiments, lipids wherein the fatty acyl chains are replaced by fatty ether chains, so called 'ether lipids', are utilized in lieu of either the neutral phospholipid, the PEG-ylated phospholipid or both. They may also be employed as part of a mixture of phospholipids and lipids employed to stabilize the emulsion. The inventors have discovered that careful selection of the lipids may be employed to create stable emulsions of dodecafluoropentane (DDFP) and fluorocarbons and these afford effective transport of oxygen.

A buffer is provided that stabilizes the viscosity of the suspending medium surrounding an emulsion of a fluorocarbon material. The addition of a 0.01 M phosphate buffer stabilizes the pH. Applicants further discovered that this buffer actually functions to maintain the desired viscosity of Applicants' emulsion.

Furthermore, the buffer prevents an increase in the osmotic concentration of the formulation over time. Due to its ability to organize in aqueous solution and form a quasi lattice-work to support the emulsion droplets, in certain embodiments sucrose (30% w/v) is employed as a viscosity enhancer. When a sucrose molecule hydrolyzes, it becomes a molecule of fructose and a molecule of glucose; thus, potentially doubling the overall solute concentration of the aqueous phase. In addition, fructose and glucose destabilize the sucrose scaffolding which in turn decreases the viscosity of NVX-108. Maintaining the integrity of the initial sucrose "structure" positively contributes to the physical stability of the formulation by maintaining a constant osmotic concentration, and the inherent molecular lattice that is specific to sucrose in water, to provide a 2-fold increase in viscosity.

The fluorocarbon used in the system may be a straight chain or a branched perfluorocarbon, fluorohydrocarbon, halogenated fluorocarbon, halogenated partially fluorinated hydrocarbon or a tri-perfluoroalkylamine. The fluorinated materials may contain from about 4 to about 16 carbons. Preferred fluorocarbons include perfluoropentane, perfluorohexane, perfluoroheptane, perfluorooctane, perfluorononane, perfluoro-tributylamine, perfluorodecane and perfluorooctylbromide. Particularly preferred perfluorocarbons include perfluoropentane, perfluorohexane and perfluorooctane with perfluoropentane most preferred. Mixtures of the abovementioned fluorine-containing compounds may be employed to optimize the oxygen carrying and delivery properties of the emulsion and the stability of the emulsion.

The PEGylated phospholipid emulsions are useful for oxygen delivery and treatment of oxidative stress and biomedical conditions characterized by decreased oxygen. They may also be used in vitro for cell culture applications. For use in cell culture the emulsion may be pre-loaded with oxygen, e.g. by bubbling oxygen through the emulsion. For treatment of conditions in vivo they are preferably administered IV but may also be administered into other body cavities including the trachea, the lungs, orally, rectally and dermally. The emulsions are administered IV to treat conditions of stroke, heart attack, radiation sensitization of hypoxic tumors, to sensitize cancer to chemotherapy, traumatic brain injury, hemorrhagic shock, spinal cord injury, sickle cell crisis, wound healing, cardiogenic shock, ARDS (lung damage), septic shock, organ transplantation and other ischemic conditions. They may also be administered to aid in removal of carbon monoxide in carbon monoxide poisoning.

The following examples are presented to further illustrate to persons skilled in the art how to make and use the invention. These examples are not intended as a limitation, however, upon the scope of the invention.

Example 1

Preparation of Saturated Lipid Emulsion

A 100 mL volumetric flask was filled to the mark with water. The flask was emptied into a beaker containing a magnetic stir bar and the beaker was marked at the meniscus. The beaker was emptied after which glycerol (5 mL) and water for injection (referred to henceforth as WFI, 80 mL) was placed in the beaker which was then placed on a hotplate-stirrer and heated to 55° C. for 15 minutes. NaCl (488 mg), NaH2PO4 (234 mg) and Na2HPO4 (216 mg) were added to the stirring glycerol/WFI mixture. This was stirred until the salts dissolved. In a second beaker on a second hotplate-stirrer, propylene glycol (10 mL) was added. The propylene glycol was stirred and heated to 55° C. Dipalmitoylphosphatidylcholine ("DPPC") (Avanti Polar Lipid cat#850355P, 114.24 mg) was added to the stirred propylene glycol until allowing the DPPC dissolved. Then dipalmitoylphosphatidylethanolamine with covalently linked poly(ethylene glycol) having a number average molecular weight of about 5000 Daltons ("DPPE-PEG-5000, Avanti Polar Lipid cat#880200P, 133.61 mg) was added to propylene glycol and stirred until its dissolution. Then the solution of the phospholipids in propylene glycol was added to previously prepared aqueous solution of glycerol, phosphate buffer and sodium chloride. Aliquots of the resulting hot aqueous mixture were used to rinse all the lipid mixture into the beaker. Then the stirred solution was diluted to the previously made mark on the beaker with WFI and was stirred for 30 minutes. The lipid mixture was removed from hotplate-stirrer and the pH was adjusted to 6.5±0.5 using 1M HCl and/or 1M NaOH. The resulting solution of suspended lipid mixture was cooled to room temperature. During the cooling period, chiller lines and tubing were attached to the homogenizer and pressure vessel with the chiller set to 4° C. and cooling was initiated, and bags of ice were placed around the homogenizer.

The cooled lipid mixture was poured into the homogenizer sample cylinder. DDFP (in a graduated cylinder) was removed from the freezer. A 2 mL of aliquot of DDFP at freezer temperature was quickly added to the homogenizer's sample cylinder. The cylinder was sealed and homogenization was conducted at 14,000 psi for 30 minutes. The homogenizer was stopped and the flow directed from the homogenizer to the pressure vessel. The pressure vessel was vented. The homogenizer was restarted and all of the emulsion transferred to the pressure vessel. The homogenizer was stopped and the vent closed and the 3-way valve closed. The tubing was removed and the pressure vessel transferred to the filling hood. The gas and filler tubing was connected to the pressure vessel. The pump was primed and, using a graduated cylinder and an Erlenmeyer flask calibrated to dispense 7.5 mL aliquots. The vials were filled with the solution of emulsified DDFP (henceforth referred to as DDFPe) and immediately capped and crimped.

Example 2

Utility of Buffer

A lipid suspension of DDFP was prepared as above except that it was prepared in a 30% weight/volume sucrose solution yielding a viscosity of about 2.8 mPas. Two samples were prepared, one with a buffer at pH 7.0 using 0.01 M sodium phosphate and the other without a buffer. The sucrose broke down more quickly in the solution without buffer; the sucrose concentration was reduced and fell with a corresponding rise in the concentrations of glucose and fructose in the unbuffered solution vs the buffered emulsion.

Example 3

Preparation of Unsaturated Lipid Emulsion

A stirred solution of aqueous NaCl, phosphate buffer and glycerol was prepared as in the procedure of Example 1 and kept at 55° C. Propylene glycol was stirred at 55° C. in a separate beaker and 18:1 (Δ9-Cis) phosphatidylcholine (DOPC) specifically 1,2-dioleoyl-sn-glycero-3-phosphocholine (Avanti Polar Lipids Catalog #850375, 114.24 mg) was added with continued stirring. When the DOPC was dissolved, 18:1 PEG5000 PE 1,2-dioleoyl-sn-glycero-3-phosphoethanolamine-N-[methoxy(polyethylene glycol)-5000]-ammonium salt Avanti Polar Lipids catalog #880230, 133.61 mg) was added and the mixture was stirred until the added lipid dissolved. Then the solution of the phospholipids in propylene glycol was added to the stirred aqueous solution of salts, glycerol and WFI. Aliquots of the resulting hot aqueous mixture were used to rinse all the lipid mixture into the beaker. The stirred aqueous suspension of phospholipids was diluted to the mark with WFI as in Example 1. The lipid mixture was removed from the hotplate-stirrer, allowed to cool to room temperature followed by adjusting the pH to 6.5±0.5 using 1M HCl and/or 1M NaOH. During the cooling period chiller lines and tubing were attached to the homogenizer and pressure vessel. Chilling of the pressure vessel to 4° C. was initiated and bags of ice were placed around homogenizer.

The cooled lipid mixture was poured into the homogenizer sample cylinder. DDFP (in a graduated cylinder) was removed from the freezer. A 2 mL of aliquot of DDFP at freezer temperature was quickly added to the homogenizer's sample cylinder. The cylinder was sealed and homogenization was conducted at 14,000 psi for 30 minutes. The homogenizer was stopped and the flow directed from the homogenizer to the pressure vessel. The pressure vessel was vented. The homogenizer was restarted and all of the emulsion transferred to the pressure vessel. The homogenizer was stopped and the vent closed and the 3-way valve closed. The tubing was removed and the pressure vessel transferred to the filling hood. The gas and filler tubing was connected to the pressure vessel. The pump was primed and, using a graduated cylinder and an Erlenmeyer flask calibrated to dispense 7.5 mL aliquots. The vials were filled with the solution of emulsified DDFP (henceforth referred to as DDFPe) and immediately capped and crimped.

Example 4

Preparation of Mixed Chain Emulsion

A stirred solution of aqueous NaCl, phosphate buffer and glycerol was prepared as in the procedure of Example 1 and kept at 55° C. Propylene glycol was stirred at 55° C. in a separate beaker and 16:0-18:1 PC, specifically, 1-palmitoyl-2-oleoyl-sn-glycero-3-phosphocholine (Avanti Catalog #850457, 114.24 mg) was added with continued stirring. When the phospholipid dissolved, 18:1 PEG5000 PE 1,2-dioleoyl-sn-glycero-3-phosphoethanolamine-N-[methoxy (polyethylene glycol)-5000] ammonium salt (Avanti Polar Lipids catalog #880230, 133.61 mg) was added and the mixture was stirred until the added lipid dissolved. Then the solution of the phospholipids in propylene glycol was added to the stirred aqueous solution of salts, glycerol and WFI. Aliquots of the resulting hot aqueous mixture were used to rinse all the lipid mixture into the beaker. The stirred aqueous suspension of phospholipids was diluted to the mark with WFI as in Example 1. The lipid mixture was removed from the hotplate-stirrer, allowed to cool to room temperature followed by adjusting the pH to 6.5±0.5 using 1M HCl and/or 1M NaOH. During the cooling period chiller lines and tubing were attached to the homogenizer and pressure vessel. Chilling of the pressure vessel to 4° C. was initiated and bags of ice were placed around homogenizer.

The cooled lipid mixture was poured into the homogenizer sample cylinder. DDFP (in a graduated cylinder) was removed from the freezer. A 2 mL of aliquot of DDFP at freezer temperature was quickly added to the homogenizer's sample cylinder. The cylinder was sealed and homogenization was conducted at 14,000 psi for 30 minutes. The homogenizer was stopped and the flow directed from the homogenizer to the pressure vessel. The pressure vessel was vented. The homogenizer was restarted and all of the emulsion transferred to the pressure vessel. The homogenizer was stopped and the vent closed and the 3-way valve closed. The tubing was removed and the pressure vessel transferred to the filling hood. The gas and filler tubing was connected to the pressure vessel. The pump was primed and, using a graduated cylinder and an Erlenmeyer flask calibrated to dispense 7.5 mL aliquots. The vials were filled with the solution of emulsified DDFP (henceforth referred to as DDFPe) and immediately capped and crimped.

Dynamic light scattering measurements can be employed to characterize the lipid emulsions prepared as described above and using other total lipid concentrations and components. For example the saturated lipid emulsion of DDFP such as that of Example 1 is diluted by addition of 7 drops of the emulsion into approximately 3 mL of a diluent consisting of propylene glycol (10% v/v), glycerol (5% v/v) and WFI (85% v/v) which has been added to a sample cuvette appropriate for a Nicomp 380 Particle Sizer (Particle Sizing Systems, Port Richey, Fl.). The cuvette is capped and gently inverted 4-5 times and placed into the sample chamber. Then the sample is allowed to equilibrate to a chamber temperature of 19° C. After equilibration the sizing measurement is conducted using the following parameters: Refractive index 1.33, Liquid viscosity 1.99 CP, Intensity set point 250 Hz, External Fiber angle 90°, Cum % 80%.

The intensity weighted particle size data can obtained in ascii form and graphed in a data handling program such as Microsoft Excel™. Typical data for emulsions of DDFP prepared using saturated lipid mixtures such as described in Example 1, of a range of total lipid concentrations, are recited in Table 1, below. The data for Samples 1, 2, and 3, are given in nanometers.

Figure 2:
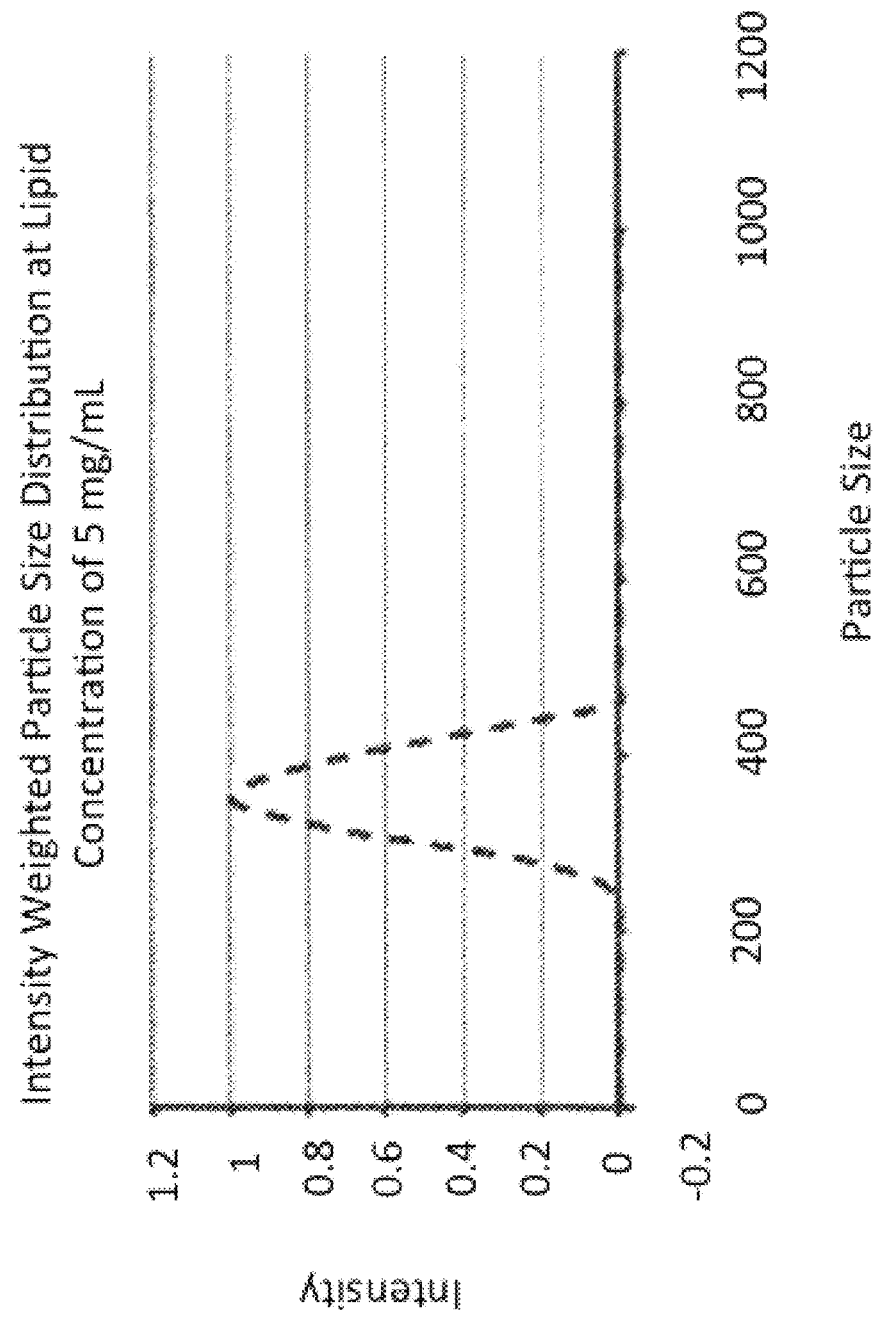
FIG. 2 graphically recites a particle size distribution for Applicants' formulation comprising a lipid concentration of about 5 mg/mL.
Figure 3:
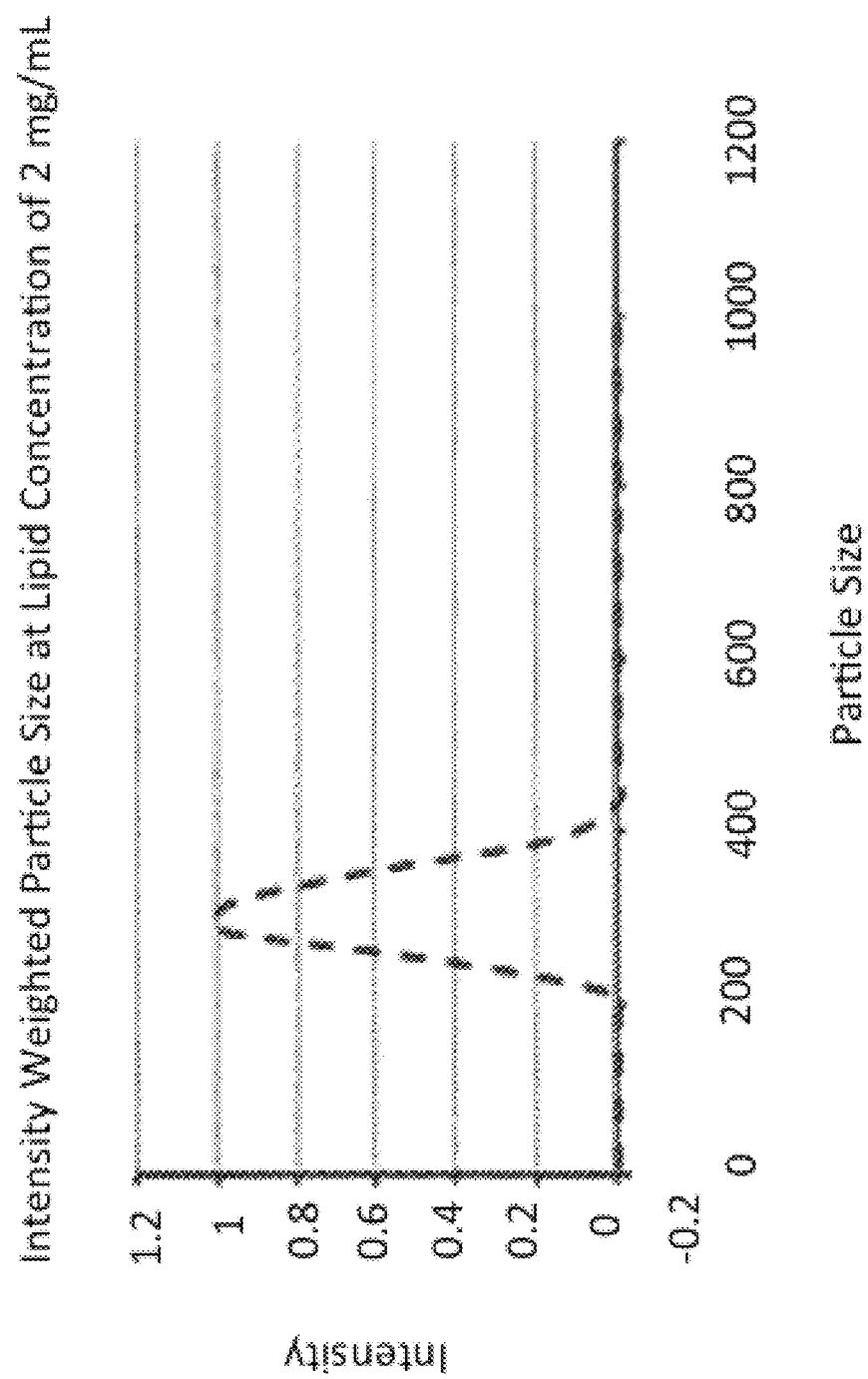
FIG. 3 graphically recites a particle size distribution for Applicants' formulation comprising a lipid concentration of about 2 mg/mL.
Figure 4:
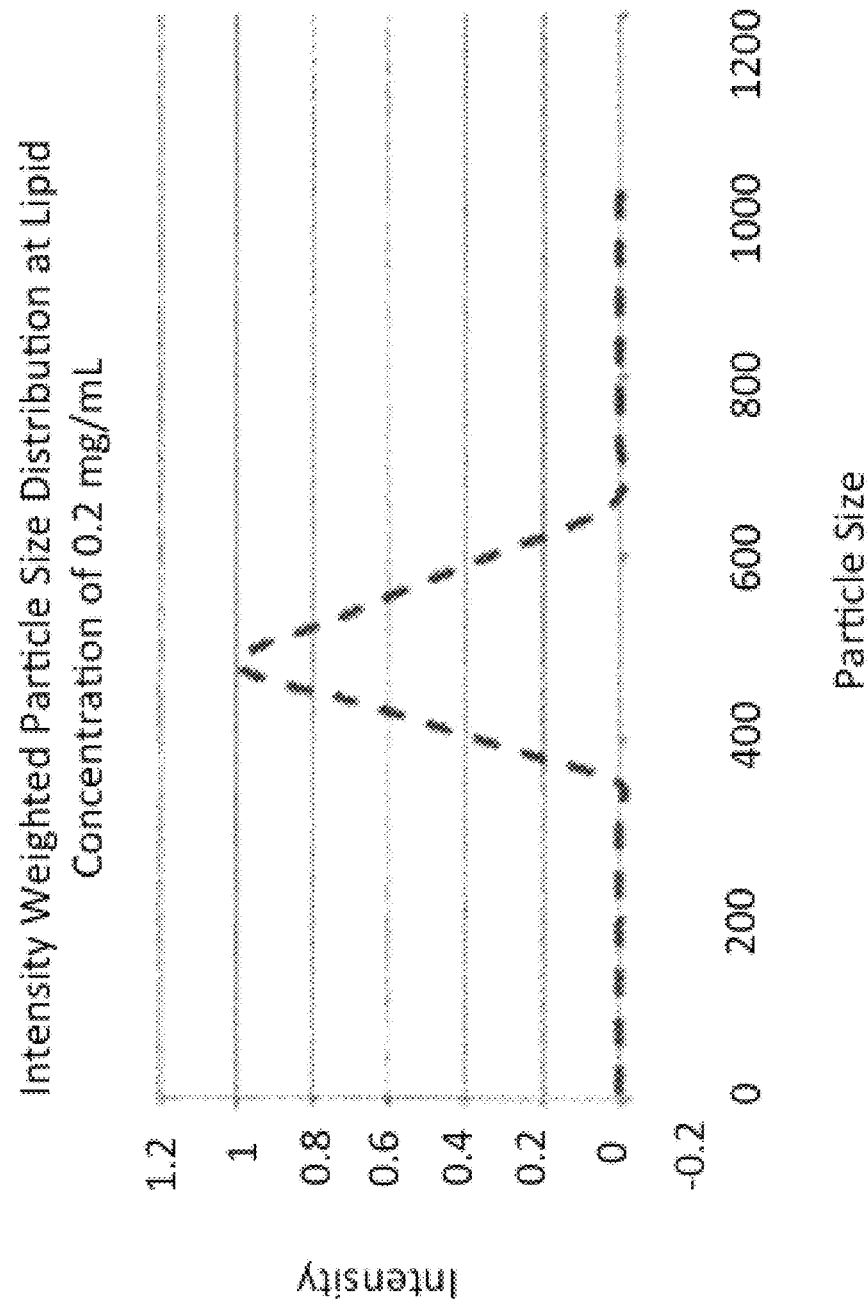
FIG. 4 graphically recites a particle size distribution for Applicants' formulation comprising a lipid concentration of about 0.2 mg/mL.

FIGS. 1, 2, 3, and 4, graphically show particle size distributions for Applicants' compositions having a lipid concentration of 10 mg/ml, 5 mg/ml, 2 mg/ml, and 0.2 mg/ml. In these graphs of FIGS. 1, 2, 3, and 4, lipid concentration refers to the lipid concentration before dilution of the emulsion prior to particle size analysis.

TABLE 1

|  | Lipids (mg/mL) | | | |
| --- | --- | --- | --- | --- |
|  | 10 | 5 | 2 | 0.2 |
| Sample 1 | 297.5 | 330.9 | 304.6 | 480.2 |
| Sample 2 | 323.5 | 361.5 | 311.1 | 485.1 |
| Sample 3 | 324.6 | 373.1 | 318.9 | 551.4 |
| Average | 315.2 | 355.2 | 311.8 | 505.6 |
| Std. Dev. | 15.3 | 21.8 | 7.5 | 39.8 |
| Rel Std. Dev. (%) | 4.9 | 6.1 | 2.3 | 7.9 |

While the preferred embodiments of the present invention have been illustrated in detail, it should be apparent that modifications and adaptations to those embodiments may occur to one skilled in the art without departing from the scope of the present invention.

We claim:

1. An oxygen therapeutic composition, comprising:
   water;
   a perfluorocarbon material selected from perfluoropentane and perfluorohexane;
   a buffer; and
   dipalmitoylphosphatidylcholine and/or dipalmitoylphosphatidylcholine mixed with dipalmitoylphosphatidylethanolamine with covalently linked poly(ethylene glycol) (PEG) with molecular mass 5000;
   wherein:
   the buffer comprises $NaH_2PO_4$ and $Na_2HPO_4$ and stabilizes a pH of the composition at between about 6.5 to about 7.5; and
   the composition comprises a viscosity of about 2.0 to about 3.5 mPas.

2. The composition of claim 1, comprising dipalmitoylphosphatidylcholine.

3. The composition of claim 1, wherein said composition is homogenized to form an emulsion.

4. The composition of claim 3, comprising dipalmitoylphosphatidylcholine.

* * * * *